United States Patent [19]

Reading, III

[11] 4,261,371
[45] Apr. 14, 1981

[54] METHOD AND APPARATUS FOR DETERMINING OVULATION IN FEMALE MAMMALIA

[76] Inventor: William H. Reading, III, 2033 E. Jonice Way, Phoenix, Ariz. 85022

[21] Appl. No.: 870,547

[22] Filed: Jan. 18, 1978

[51] Int. Cl.³ .............................................. A61B 5/05
[52] U.S. Cl. .................................................. 128/738
[58] Field of Search ............. 128/2 R, 2.05 R, 2.05 T, 128/2.06 R, 2.06 A, 2.06 F, 2.1 Z, 639–644, 738; 324/71 R, 72, 72.5

[56] References Cited

U.S. PATENT DOCUMENTS

| | | | |
|---|---|---|---|
| 3,297,020 | 1/1967 | Mathiesen | 128/2 R |
| 3,620,208 | 11/1971 | Higley et al. | 128/2.06 E |
| 3,834,373 | 9/1974 | Sato | 128/2.1 E X |
| 3,868,947 | 3/1975 | Holsinger | 128/2.06 E |
| 3,920,003 | 11/1975 | Ash et al. | 128/2.1 Z |
| 3,920,969 | 11/1975 | Berglas | 128/2.1 E X |
| 3,924,609 | 12/1975 | Friedenberg et al. | 128/2.1 R |
| 4,105,023 | 8/1978 | Marchese et al. | 128/2.06 F X |

OTHER PUBLICATIONS

Caldwell, W. M. et al., "A Wide-Range Linear Beat-By-Beat Cordiotachometer", Med. & Biol. Engr., vol. 8, 1970, pp. 181-185.

Ray, C. D., "Biomedical Engineering", Yrbk Publ., Chicago 1974, pp. 1000–1014.

Primary Examiner—Robert W. Michell
Assistant Examiner—Francis J. Jaworski
Attorney, Agent, or Firm—Leitner, Palan, Martin & Bernstein

[57] ABSTRACT

A method and apparatus for measuring bio-electrical potential in female mammalia to determine ovulation.

The apparatus includes a first and second container operable to contain an ionic medium and to receive in one container at least one finger of one hand of a test subject and a first active probe and to receive in the other container at least one finger of the other hand of the test subject and a second active probe. An electrical network for measuring electronic potentials in the millivolt range is connected to the active probes and functions to measure increases in potential emitted by the test subject upon ovulation.

The method includes the steps of inserting at least one finger of one hand of a test subject into a first container along with a first active probe, inserting at least one finger on the other hand of the test subject into a second container along with a second active probe and measuring ionic potential changes within the test subject through ionic current flow through the ionic medium and electron flow through the active probes and measuring networks. Digital circuits respond to the measured potential of the test subject to display the potential while accumulating and averaging several potential readings.

17 Claims, 5 Drawing Figures

METHOD AND APPARATUS FOR DETERMINING OVULATION IN FEMALE MAMMALIA

BACKGROUND OF THE INVENTION

This invention relates to a method and apparatus for measuring bio-electrical potential changes in female mammalia to determine ovulation and constitutes an improvement over applicant's prior U.S. Pat. No. 3,924,609 entitled DETECTOR DEVICE AND PROCESS FOR DETECTING OVULATION.

Numerous efforts have been made in the art to accurately determine the timing and fact of ovulation as an aide for achieving or avoiding fertilization of an ovum by the timed presence or absence of male spermatozoa. These prior efforts include, for example, measurement of cyclical body temperatures, cytological evaluation of exfoliated cells in vaginal mucosa, endometrial biopsy, biochemical, including hormone change, analysis, and it has even been suggested to measure vaginal potential changes over a total ovulation cycle. See Yale J. Biol. & Med. 21: 249-253 (1949). These prior efforts exhibit inadequate sensitivity to low D.C. potentials to serve the purpose of easy, dependable, and accurate measurement, sufficient to provide an adequate, reliable indication at a remote measurement point of the deep-seated fact and timing of ovulation occurrence.

From initial studies on infrahuman mammals, followed by direct studies on the human female, basic research dating back to the mid 30's established a correlation between the physiological phenomenon of menstruation and ovulation and bio-electric body potentials.

During the menstruation cycle of a human female the ovum grows or ripens into a primary follicle each month, increasing many fold in size with a corresponding increase in the number of cells surrounding each ovum in several distinct tissue layers, the follice cavity being filled with liquid or follicular fluid in which the ovum is eccentrically disposed. Chromosome changes occur in the ovum and the structure of the follicle changes until spontaneous discharge of the ovum and fluid contents into the uterus in anticipation of fertilization. The cellular process leading to these changes is active with the elaboration of ovulatory enzymes which also affects the collagen supporting network of the follicle and ovary. A consequence is that for some 5 or 6 days before ovulation, the rapid growth of the ovum proceeds to the acutual event of ovulation. The follicle bursts and sweeps the ovum and fluid into the fallopian tubes ultimately to the uterus. That rupture of the follicle tissue in the presence of the streaming follicular fluid produces a predictable small potential which can be calculated. See, Electronstatics of Biological Cell Membranes, pages 83-106, R.M. Friedenberg, 1967 by North Holland Pub. Amsterdam.

Each phase of the ovulatory cycle, beginning with the periodic ripening of the follicle and ovulation through a final expulsion of the ovum from the uterus, signals small measurable electrostatic potentials variably developed and steadily rising with the succeeding steps of the process and which achieve a sharp peak of D.C. potential output at about the time of ovulation, then reducing, providing a direct current potential whose measurement allows the identification of the phase and timed sequence of this physiological event. The potentials of the cycle will change from a normally minus to a plus potential as the event proceeds reachng a maximum during ovulation. The ovum proceeds through the fallopian tubes and then to the uterus where it remains for about 12 hours awaiting fertilization at decreased potential; and after explusion, the potential slowly returns to a normal, minus, i.e., opposite polarity value.

In one case study, Messers Burr, Musselman, Banton and Kelly demonstrated that a positive bio-electric increase in potential occurred during ovulation in a human female on the 21st day of the menstrual cycle, which was confirmed at laparotomy. Burr et. al., BIO-ELECTRIC CORRELATES OF HUMAN OVULATION, Yale J. Biol. and Med. 10: 155, 1937.

Numerous electronic detecting instruments have been proposed to determine the timing of ovulation. One such prior known device comprises a vaginal probe consisting of two similar dual metal electrodes physically supported on an enlongated electrical insulating body with one of the electrodes disposed adjacent one end of the body and the other electrode disposed a further position down the length of the support body. In operation, the probe is connected to an indicator device, such as a high impedance FET balanced differential amplifier which is used to drive a meter. The probe is inserted into the vagina of a subject, until the last most electrode makes contact with the vaginal opening. This unit measures the electrochemical transformations in vaginal fluid to detect ovulation.

Instruments of this general design have proven to be somewhat inconvenient for the test subject and do not provide a remote measurement capability as desired.

A significant theoretical advance was achieved by the conception of applicant's prior detector device disclosed in U.S. Pat. No. 3,924,609. For a complete discussion of applicant's prior invention, the reader's attention is directed to this patent disclosure. Briefly, however, with applicant's prior system, a subject to be tested would grasp an electrode in each hand. Bio-electrical changes in potential of the subject were designed to be detected in the millivolt range by detection circuitry including a high impedance two section RC filter network, a differential to single ended operational amplifier, and active amplification networks.

The foregoing combined circuitry exhibited the characteristics of extremely high input impedance and high common mode rejection combined with isolation and filtration to indicate and measure low D.C. ovulation potentials.

Although applicant's prior detecting apparatus reflects at least a theoretical advance in the art, it has been determined that direct physical contact between the subject and the hand held electrodes imparts body electron contamination to the ionic bipotential signals being measured. Further, applicant's prior invention relied upon very high input impedances, in the range of $10^{10}$ ohms or greater, in conjunction with passive filtering to reduce the effects of AC signals which may be present. With such high input impedances, however, difficulties exist with respect to signal contamination from ambient sources such as domestic power lines, radios, business machines etc. Moreover high input impedances exacerbate the problems inherent in accurately balancing the system.

The difficulties suggested in the preceding are not intended to be exhaustive, but rather are among many which may tend to reduce the effectiveness and user satisfaction of prior ovulation measuring devices. Other noteworthy problems may also exist; however, those presented above should be sufficient to demonstrate that methods and apparatus for accurately and reliably detecting the timing of ovulation in female mammalia will admit to worthwhile improvement.

OBJECTS OF THE INVENTION

It is therefore, a general object of the invention to provide a novel method and apparatus for measuring the bio-electrical potential in female mammalia to determine ovulation which will obviate or minimize difficulties of the type previously described.

It is further a general object of the invention to provide a novel method and apparatus for measuring the bio-electrical potential in female mammalia wherein the ease, accuracy, and reliability of remote measurement is enhanced with respect to previously known systems.

It is a specific object of the invention to provide a novel method and apparatus to determine ovulation wherein body electron contamination of biopotential ionic signals is minimized.

It is another object of the invention to provide a novel method and apparatus for measuring biopotential ionic signals to determine ovulation wherein environmental noise on the measured signal such as power line, radio, typewriter noise, etc., is minimized.

It is yet another object of the invention to provide a novel method and apparatus for measuring ionic biopotential to determine ovulation wherein $10^{10}$ ohm or greater input impedances of previously known measuring instruments may be reduced while continuing to measure ionic current in the $10^{-8}$ or $10^{-9}$ ampere range.

It is still another object of the invention to provide a novel method and apparatus for measuring ionic biopotential to determine ovulation wherein the system may be facilely and accurately balanced between a pair of measuring probes to provide an improved overall system stability.

It is a further object of the invention to provide a novel method and apparatus for measuring ionic biopotential to determine ovulation which will minimize capacitive effects at the input measuring probes.

It is yet a further object of the invention to provide a novel method and apparatus for measuring ionic biopotential to determine ovulation wherein common mode interference in the measuring instrument is minimized.

It is still a further object of the invention to provide a novel method and apparatus for measuring ionic biopotential to determine ovulation wherein low frequency noise of one cycle or less on the measured signal may be eliminated.

BRIEF SUMMARY OF THE INVENTION

A method and apparatus, according to a preferred embodiment of the invention, which is intended to accomplish at least some of the foregoing objects, comprises insertion of a test subject's finger of one hand into an ionic medium within a first container and insertion of the test subject's finger of the other hand into an ionic medium within a second container.

The ionic medium may be a saline liquid solution, paste or other substance capable of supporting ionic current and which contains free ions similar to those found in body fluid and of the same general concentration.

A first active probe is inserted into the first container and a second active probe is inserted into the second container. Each active probe is provided with a metallic element having a surface area which contains a metallic form of the ion contained within the ionic medium. Examples of operative metallic salt probes or probes formed from the metallic salt only include Ag-AgCl or CuCl.

The active probes convert ionic current flow from the test subject's body to electron flow. This electron flow is input to preamplifiers forming a portion of the active probes which converts a high input impedance to a relatively low output impedance for further signal processing.

The signal from the preamplifiers may initially be double-ended and is then changed to a single ended signal referenced to system ground through a differential amplifier. The signal is then quantized and digitally filtered in a novel digital filter driven by a specially constructed clock generator powered from the output of the active probes, which outputs contain interfering signals, particularly signals at the power line frequencies. If signal contamination is low, power line signals may be obtained directly for clock purposes.

The quantized and filtered signal may displayed and accumulated and averaged utilizing digital techniques. The finally processed signal may then displayed in one of several meaningful fashions as chosen by a user to depict bio-electric potential changes in the test subject's body which signal the occurrence of ovulation.

THE DRAWINGS

Other objects and advantages of the present invention will become apparent from the following detailed description of a preferred embodiment thereof taken in conjunction with the accompanying drawings, wherein.

DETAILED DESCRIPTION

Figure 1:
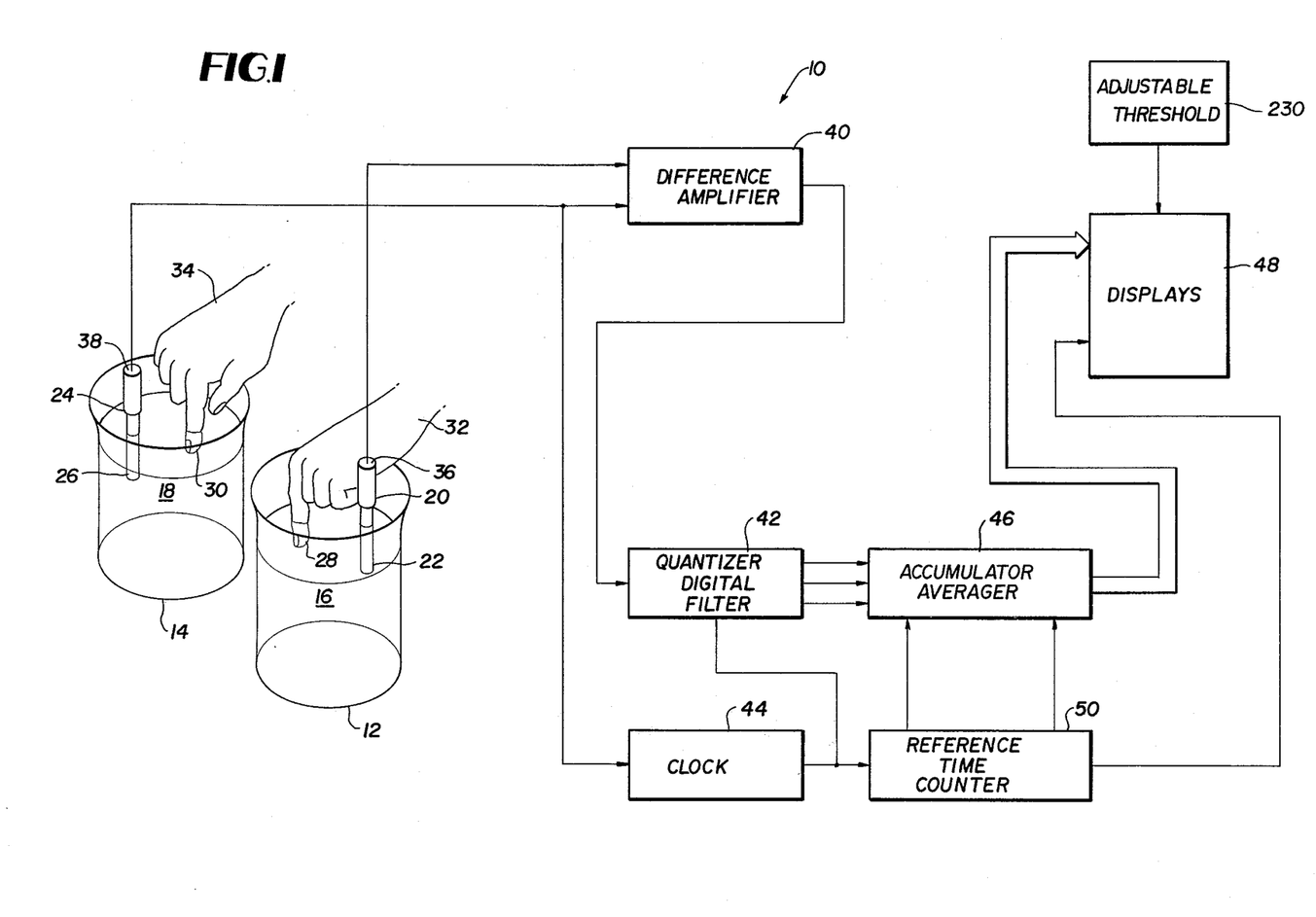
FIG. 1 is a system block diagram of an ovulation determining device in accordance with the invention including a pair of salt solution beakers, a difference amplifier, a quantizer, digital filter and clock generator, an accumulator averager and display.

Referring now to the drawing wherein like numerals indicate like parts, and particularly to FIG. 1, there will be seen a system 10 for measuring ionic bioelectrical potential changes in a test subject to determine the timing of ovulation within the subject.

The system 10 includes a first container or beaker 12 and a second container or beaker 14 operable to hold ionic mediums 16 and 18, respectively. The ionic mediums may be in the form of solution, paste or other substance capable of supporting ionic currents and shall contain free ions similar to those found in body fluid and of the same general concentration.

A first active probe 20 includes a metallic element 22 immersed in the ionic medium 16. A second active probe 24 includes a metallic element 26 immersed in the ionic medium 18. The metallic elements 22 and 26 comprise metal-metallic salt probes or probes formed from the metallic salt only. Examples of probes which are suitable for use in the subject invention comprises Ag-AgCl or Cu-CuCl.

The containers 12 and 14 are sized to be large enough to receive the metallic electrodes 22 and 26 and at least one finger, such as index fingers 28 and 30, of a subject's hand 32 and 34, respectively. The exact position of the subject's finger within a beaker is not critical although as depicted in FIG. 1 it is necessary that the finger be spaced from direct physical contact with the metallic elements. Accordingly, bio-electric potential variances within the test subject which are ionic are picked-up by the metallic elements 22 and 26 and converted to electron flow for processing and measurement.

Each of the active probes 20, 24, includes an impedance converting preamplifier 36 and 38 mounted directly adjacent the metallic elements 22 and 26. These preamplifiers present a high input impedance and a low output impedance and function primarily as impedance converters. The low output impedance presented by preamplifiers is significantly advantageous for such an impedance is more suitable for working with conventional electronics and is less subject to environmental noise as will be discussed more fully below. The outputs from the preamplifiers 36 and 38 are fed into a difference amplifier 40 which changes the double ended signal to a single ended signal referenced to system ground for processing by the system 10. The amplifier 40 produced signal is then input to a quantizer and digital filter 42 driven by a clock generator 44 responsive to signals at the local power line frequencies, which signals may be derived from the outputs of the active probe.

The quantized and filtered signal is then fed to an accumulator and averager 46 which utilizes digital techniques to average biopotential readings over a defined time interval controlled by the reference time counter 50. The averaged signal may be input to a display unit 48 to display bio-electric activity and the existence or non-existence of ovulation as will be discussed in detail hereinafter.

Figure 2:
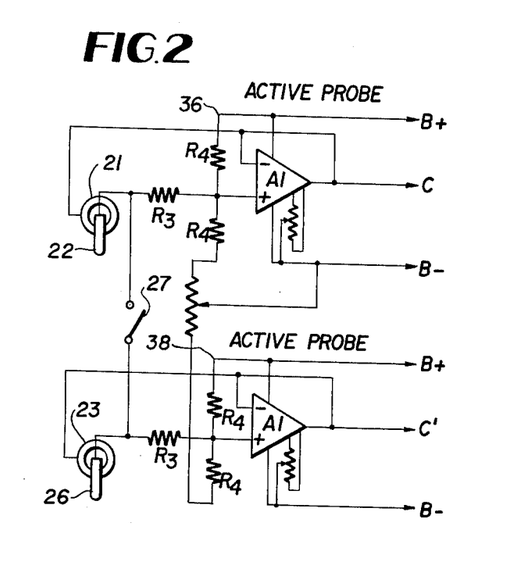
FIG. 2 is a diagram of a pair of active probes in accordance with the invention.

FIG. 2 illustrates my preferred embodiment of the active probes 20, 24 each of which is comprised of a metallic electrode 22, 26, and a preamplifier 36, 38. A shielding device in the form of a capacitor ring 21, 23 may also be provided. As mentioned hereinbefore, the probe electrodes 22, 26 are constructed of either a metallic salt or of a metal core surrounded by the metallic salt. The preamplifier, which forms a portion of each active probe, includes an operational amplifier A1 and an impedance network comprised of equal valued resistors R4. Resistor R3 of each amplifier A1 is provided to limit current flow through the test subject in the event of catastrophic failure of the preamplifier circuit. Each of the two active probes is identical. By locating the preamplifier as part of the probe assembly, problems associated with interference pick-up is drastically reduced. The interference reduction feature will be appreciated when it is understood that all electronic equipment is susceptible to electromagnetic interference from external sources. Interconnecting wires act as antennas and in the present situation the test subject herself also picks up interfering radiation such as is generated by local power lines. In the absence of expensive shielding and filtering, these interfering signals and particularly signals at the power line frequency, appear as noise in the equipment. When low level information signals are to be processed by the electronic equipment, these noise signals severely mask and distort these information signals and thus prevent accurate processing. Locating a preamplifier within the probe assembly reduces the interconnecting wires, thus reducing the opportunity for interfering signals to be picked up by the circuitry of the present invention.

The preamplifiers 36, 38 are designed to provide a high input impedance and a low output impedance, and thus produce an impedance conversion at the probes. The preamplifier high input impedance allows small changes in the test subject produced ionic current to appear as a measurable voltage across the preamplifier input. The low output impedance presented by the preamplifier allows maximum signal transfer to the digital utilization circuitry connected thereto.

This high input impedance is achieved by suitably selecting the value of resistors R4. One terminal of each of these resistors R4 is connected, respectively, to bias voltages of equal magnitude but opposite sign, with the other terminal of each of these resistors being connected to an input of the preamplifier A1. The current limiting resistor R3 provides the user protection against catastrophic failure of the equipment and may be selected to prevent any current greater than 5 micro-amps from existing in the test subject should such a failure occur.

The operational amplifier A1 may be either a high gain device, or a unity gain device, for the primary function of the preamplifier is not to provide gain but rather to provide a high input impedance and a low output impedance. It has been determined that it is most desirable to limit the magnitude of current flow through the test subject to 10 nano-amps or less in a voltage range of 100 millivolts or less. This criteria defines the input impedance. The input impedance to each of the preamplifiers, 36, 38, as seen by the test subject from the probes on, is given by twice the value of the resistor R3 plus the value of resistor R4. The value of the resistor R4 should be at least ten times the value of the resistor R3 so that for setting impedances, the value of the resistor R3 may be neglected. Under these conditions, the value of resistor R4 must be at least 10 megahoms or greater. It is to be understood that the present invention is not limited to a preamplifier maintaining its input impedance at 10 megohms, such figure being given by way of example only. It has been found that a circuit containing operational amplifiers with input impedance values from 10 megaohms to 1000 megohms work quite satisfactorily. Again, the invention set out herein is not limited to any specific input impedance value. Of significance is the fact the input impedance to the preamplifier is selected to be of such value that the preamplifier appears as a substantial load to its source so that substantially all of the input current appears across the input to the preamplifier. Under the above conditions, the preamplifier input appears to be at zero or ground potential from a voltage viewpoint but as a high impedance when viewed from a current viewpoint and small changes in current flow through the test subject appear as measurable voltage changes across the preamplifier input.

The probe electrode of each active probe may be surrounded by a capacitive guard ring 21, 23 functioning to eliminate capacitive effects. The guard ring is driven by the output from its associated preamplifier. By maintaining the guard ring at essentially the potential of its corresponding electrode, a zero electromagnetic and electrostatic field exists between the ring and the electrode thus shielding the electrode from external interference which might otherwise be picked up by the electrode.

The present invention makes use of two active probes for providing a differential measurement. Of course, for single ended measurements, a single signal probe would be used. Switch 27 in conjunction with the balance network is provided to allow for balancing of the probes prior to an actual measurement of a test subject. Balance must be adjusted both open circuit and short circuit via switch 27 and the associated balance network 28 for accurate measurement.

In operation of the active probe, ionic current flows from the test subject through the salt solution to the metallic salt of the electrode. This ionic current is converted into electron current in the metal portion of the probe which electron current flows through the currenting limiting resistor R3 to the input of a preamplifier A1. The output from the active probe is a measure of the body potential of the test subject.

By processing in solution using solution filled containers 12, 14 the surface area of the probe as well as the depth of the metal ion layer may be controlled. Further, the probes of the invention are much lower in impedance, probe impedance being affected by the surface area metal ion layer. When measuring in solution, a larger surface area of the subject is also contacted, thus reducing the impedance between the subject under test and the measurement device. Probes which are grasped in the hand or otherwise placed in direct contact with the body rely on a moisture layer developing between the body and the probe in order for ionic contact to be made. The impedance of this surface layer of moisture varies with pressure and the surface area varies with pressure. Thus an extreme range of impedances is anticipated when direct subject contact type probes are used and an extremely high input impedance device is required as suggested in my prior U.S. Pat. No. 3,924,609. The elimination of the analog filter at the probe output also allows the overall input impedance of the unit to be lowered. This is so because power line filters at 60 or 50 hertz require large resistors in order to keep the physical size of the capacitor small. This large resistance appears in series with the subject and acts as a loss to the signal appearing at the input to the preamplifier thus requiring very large, 1,000 megohms or greater unit input impedance. The apparatus of the present invention has been formed to operate at high reliability with an input impedance of only 10 megohms, one-hundredth of the input impedance of applicant's prior device.

Figure 3:
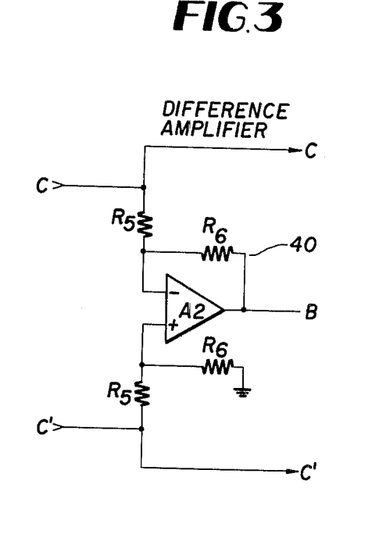
FIG. 3 is a diagram of a difference as diagrammically represented in FIG. 4.

When differential measurements are being made, the differential signals must be converted to a single ended signal. This is the function of the difference amplifier 40 illustrated in FIG. 3. The amplifier 40 receives the two signal outputs C, C' from the two active probes 20, 22, and produces a single ended output signal B referenced to ground potential. The device shown in FIG. 3 is conventionally used for this function and does not per se form a portion of the present invention. It is sufficient to say that the resistors R5, R6 in conjunction with the operational amplifier A2 form a differential amplifier circuit with the gain of the amplifier being determined by the ratio of the resistors R5, R6. For the purposes of the present invention, the actual gain of the amplifier is not critical nor is the component balance.

Figure 4:
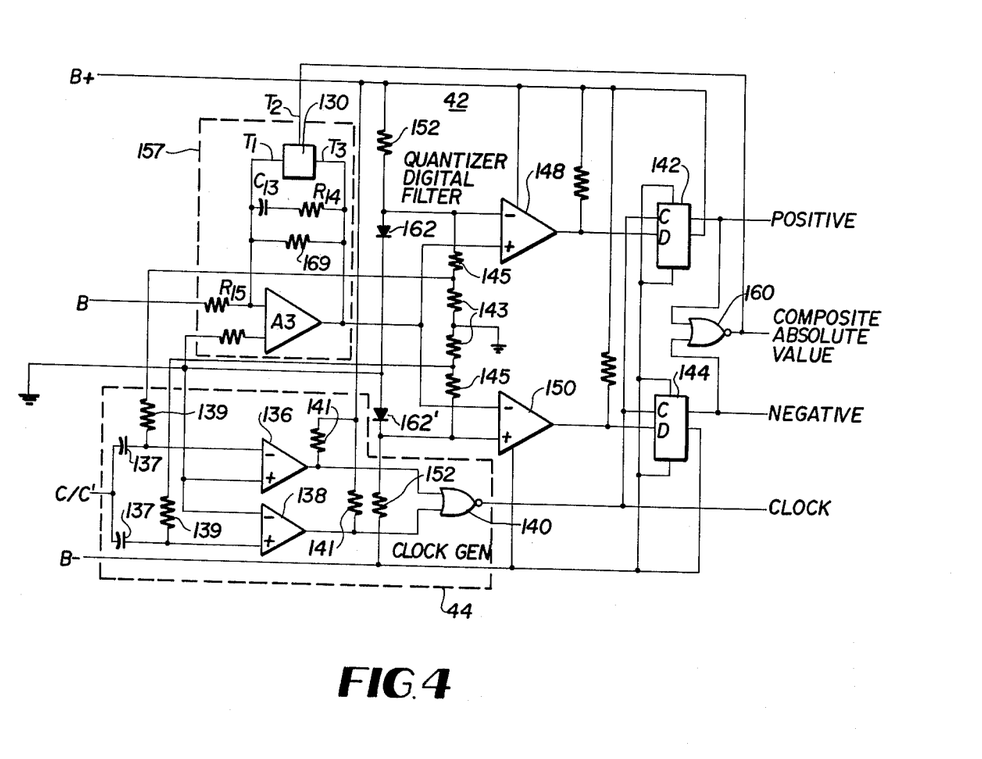
FIG. 4 is a diagram of a quantizer-digital filter and clock generator as represented in FIG. 1.

Referring now to FIG. 4, the output from the difference amplifier 40 is supplied to a quantizer digital filter 42 which functions to convert the voltage output from the difference amplifier 40 into a signal whose frequency is proportional to the input voltage. FIG. 4 also illustrates the circuit details of clock circuit 44. The quantizer digital filter 42 is basically a bidirectional voltage to frequency converter in which the pulse rate is synchronized against a clock. By careful choice of the clock, the unit becomes a digital filter providing strong attenuation of 20 Db or more to interfering signals at the clock frequency or multiples thereof. It has been determined that the strongest interfering frequency will be the power line frequency. In the United States this frequency is 60 cycles per second and for explanation purposes this frequency or multiple thereof will be selected as the clock frequency.

The clock circuit 44 includes dual comparators 136 and 138, capacitors 137, resistors 139 and 141 along with NOR gate 140. Each of the resistors 139 is connected between a resistor 145 and a resistor 143. Each resistor 143 is connected to ground while the resistors 145 are connected, respectively, through a resistance 152 to bias voltages of equal magnitude but opposite polarity. Common numerical designations for the resistors in FIG. 4 as well as in other figures herein designate common resistance values. The resistors 143 and 145 function to bias the comparators 136 and 138 in a manner to provide a pulse output of suitable width. In the preferred embodiment, the values of resistances 143 and 145 are selected so that the output pulses from the comparators 136, 138 lie between 10 and 100 microsecond. However, the actual pulse width of the clock pulses is not critical. A capacitor 137 combined with a resistor 139 function as a filter for filtering other than the 60 hertz signal from the outputs of probes 20, 24. The clock 44 thus operates in response to the 60 hertz component of the probe outputs, which component is in fact an unwanted noise signal eminating from power lines in the vicinity of the circuitry of the present invention. The positive input to comparator 136 and the negative input 138 are tied to ground. Whenever the input signal to the negative input of comparator 136 is negative with respect to ground, the output of the comparator 136 is a logic 1. Whenever the input signal to the positive input of the comparator 138 is positive with respect to ground, the output of comparator 138 is a logic 1. Thus, a logic 1 will appear at one of the two inputs to the NOR gate 140 at all times except when the inputs to the comparator circuits pass through zero volts. At each zero crossing of the input signal to the clock 44 both inputs to the NOR circuit 140 appear as logic 0 producing a logic 1 at its output. In this manner a logic 1, or clock pulse is produced for each zero crossing of the input signal to the clock circuit. For a 60 hertz input signal, a clock signal at the rate of 120 pulses per second is produced. These clock signals are utilized by the flip flops 142 and 144 of the digital filter and the accumulator-averager 46 of the invention as will hereinafter be explained.

The digital filter 42 is comprised of an integrating circuit 157, dual comparators 148, 150, flip-flops 142, 144 and OR gate 160. The integrator 157 includes an operational amplifier A3, a series connected circuit comprised of resistors R14 and capacitor C13 connected in parallel to a resistor 169, an active switching device 130 and resistor R15. The integrating time constant is determined by the values of capacitor C13 and resistor R15. The resistor R14 functions as a current limiting resistor. The resistor 159 is used to prevent latch up and is selected to be large compared with the impedance provided by the capacitor C13. The overall function of the network is to provide a maximum pulse value. Predetermined levels may be set digitally for digital displays using standard comparator techniques.

Figure 5:
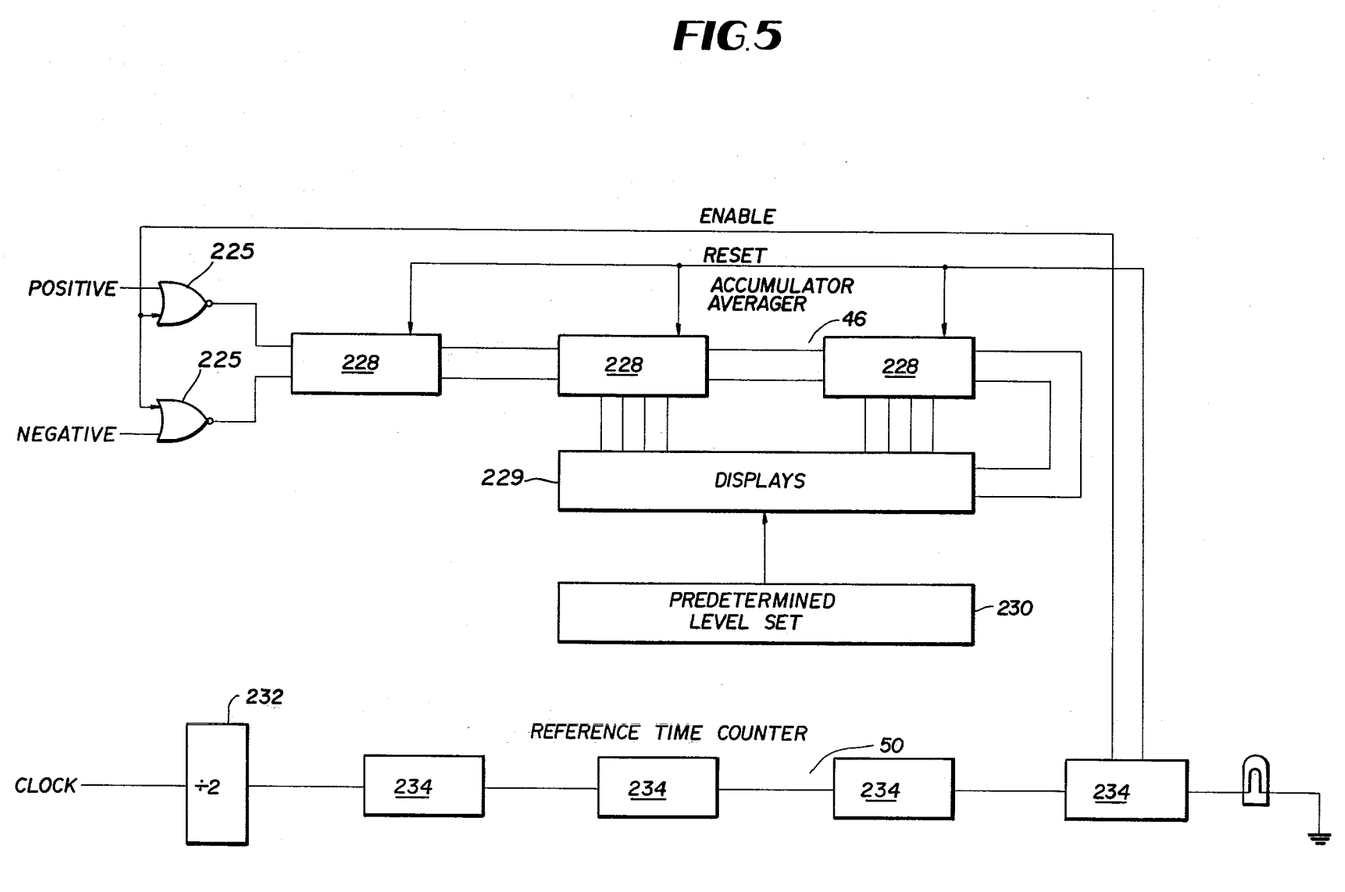
FIG. 5 is a diagram of an accumulator, time averager and display depicted in FIG. 1.

Referring more specifically to the counter chain 228, if the full scale capability of a quantizer 42 is N levels, then the accumulator of FIG. 5 must be able to store N bits, which N bits represent full scale. If M readings are to be averaged, then the overall length of the accumulator must be M+N bits. The accumulator, because of its algebraical nature, will provide a value plus polarity signal to displays 229 at the end of a complete measurement cycle. The length of a measurement cycle is determined by the reference timed counter composed of frequency dividers 232 and 234. The divider 232 produces a 60 pps output in response to 120 pps signals. This 60 pps clock signal is furthered divided in the divider chain 234 which is a counter chain 2 (M+N) bits long. The size of the reference time counter is determined in part by the fact that there are two clock pulses for each informational quantized bit. To insure the actual reading taken is not the initial reading, an added counter section may be placed at the end of the reference time counter 234. This technique allows the user to take P readings in sequence. The data from each reading may be displayed. The accumulator-averager 46 may be reset at the end of each display until the desired number of readings has been reached. In this manner the highest and lowest reading in a set P may be eliminated and the normal P-2 reading retained.

The operation of the accumulator average 46 may be explained as follows:

Assume that the actual biopotential to be measured is 6 millivolts, that full scale for the unit is 100 millivolts and that the quantizer produces 1 count per millivolt at full scale. With the primary interference signal at 60 hertz, the clock signal is at 120 pps and the output from counter 232 produces 60 counts per second. The reference counter 234 is set for 1,000 counts or a total of 10 periods. If the actual potential is to be determined at less than full scale, the quantizer will produce a count given by E potential actual divided by E potential full scale times the maximum count rate. At 6 millivolts this would be 1 count per every sixteen 60 pps clock cycles. In the time required to accumulate 1,000 counts of the reference counter 234, the accumulator will accumulate 60 counts. To average over the 10 periods, one divides this 60 pulses by 10. This is analogous to dropping the last digit of the accumulator and therefore the reading becomes 6 counts. In other words, division is accomplished by selection of display to be in agreement with the radix of the number system and then by choosing the total number of periods to be averaged over to be associated with the radix, thereby reducing division to displacement of the decimal point in the display systems.

There has been disclosed a novel device for determining ovulation in female mammalia which device makes use of unique digital techniques to filter and quantize analog signals representing the test subject's bio-potential. The quantized signal may be directly displayed. In the alternative several successive potential readings may be taken and averaged to provide a more accurate reading of the actual bio-potential. Averaging of several successive measurements cancels random errors to more accurately reflect actual bio-potential of the test subject. An active probe which includes a preamplifier reduces external influence, with further interference reduction being effected using a guard ring around each probe electrode. Further improvement in measurement accuracy is realized using the unique beaker arrangement for transferring the test subject's ionic current, proportional to her bio-potential, to the units probe.

I claim:

1. An apparatus for remote measuring of the ionic bio-electrical potential of mammalian females for determining ovulation comprising:

first active probe means including a first metallic element means; and first preamplifier means mounted upon said probe adjacent said first metallic element for amplifying analog electrical signals from said first probe metallic element;

second active probe means including a second metallic element means; and second preamplifier means mounted upon said probe adjacent said second metallic element for amplifying analog electrical signals from said second probe metallic element;

first container means for holding an ionic medium and for receiving the metallic element of said first active probe means and at least one finger on one hand of a test subject in a position spaced from said metallic element;

second container means for holding an ionic medium and for receiving the metallic element of said second active probe means and at least one finger on the other hand of the test subject in a position spaced from said metallic element; and circuit means including an analog to digital quantizer-filter means for generating a probe frequency modulated output in response to an analog input signal from said first and second active probe means and clock means for generating a pulse signal output having a frequency proportional to the frequency of a noise produced component of said analog input signal connected to output leads from said first and second active probe means for measuring ionic potential differences between said active probe means to detect the occurrence of ovulation in the test subject.

2. An apparatus for remote measuring of the ionic bio-electrical potential of mammalian females as defined in claim 1 wherein:

each of said first and second preamplifier means comprises an operational amplifier and an input impedance means associated with said operational amplifier for presenting a high input impedance to said preamplifier means each of said preamplifier means having an output with a relative low impedance compared to its input impedance.

3. An apparatus for remote measuring of the ionic bio-electrical potential of mammalian females as defined in claim 2 and further comprising:

a metallic ring means electrically isolated from but surrounding each of said first and second active probe elements; and conductor means connecting the output of each of said preamplifier means to the respective one of said metallic ring means.

4. An apparatus for remote measuring of the ionic bio-electrical potential of mammalian females as defined in claim 1 wherein said circuit means includes:

differential amplifier means connected to the output of each said first and second preamplifier means for converting a double ended signal from said first and second active probe means to a single ended signal.

5. An apparatus for remote measuring of the ionic bio-electrical potential of mammalian females as defined rate out at selected full scale input for every two clock pulses. The integrator is a device with a linear transfer function and therefore, if the full scale voltage is divided into N increments, 2N clock pulses are required to define the smallest increment. In other words, the quantizer provides a relative output referenced to the clock frequency and the full scale input. The circuit is bidirectional having different output lines for negative and positive values of the input voltage as well as a composite output to provide absolute value signals.

The values selected for the components C13 and R15 are critical for the proper functioning of the digital filter. These components designate the integrator gain which is set, according to the teachings of this invention, such that at full scale input voltage the integrator output reaches threshold in a time interval less than the period of the clock pulses. Scale voltage is set equal to the voltage drop across doide 162'. This establishes the switch point for the comparators 148 and 150.

The operation of the digital filter 42 will now be explained. The input signal B which corresponds to the output from the difference amplifier 40 is applied to the input of the integrator 157. The output of the integrator 157 is coupled simultaneously to the positive input to the comparator 148 and the negative input to the comparator 150. The negative input to comparator 148 is tied to a reference voltage determined by the voltage at the anode of the diode 162 to which it is connected. Thus, the reference voltage to the negative input of the comparator 148 is a positive voltage slightly greater than ground potential, which voltage is determined by the drop across the diode 162. The positive input terminal to the comparator 150 is connected to the cathode of a diode 162 with which it is associated. Thus, a negative reference potential slightly below ground potential is applied to the positive input terminal of the comparator 150. The actual value of the reference potential to the comparator 150 is determined by the potential drop across the diode 162. The output from the comparator 148 is connected to the D or data input of flip-flop 142 while the output from the comparator 150 is connected to the D or data input of flip-flop 144. These flip-flops are clocked by the clock generator 44. It should be noted that since clock pulses exist only when the 60 hertz interfering signal passes through zero volts no interfering 60 cycle signal will pass through the flip-flops. The output from the flip-flops 142 and 144 are connected as inputs to the NOR gate 160. A bit is quantized each time the integrator output exceeds the voltage drop across a diode 162'. When a comparator 148, 150 senses that a bit has been quantized, it changes its output state logically. However, this does not have an immediate effect on the output of a flip-flop in that the flip-flop will not change states except in the presence of a clock pulse. On the next clock pulse, the new logic level designated by a comparator 148, 150 is transferred to its associated flip-flop and appears as a change in state at the output of the flip-flop. This new logic level at the output of a flip flop will activate the active switch 130 causing discharge of the capacitor C13 through the current limiting resistor R14. This discharge of the capacitor C13 will cause the comparators 148, 150 to return to their initial state and on the next clock pulse transfer this state to the flip-flops 142, 144. This state change recognized by the flip-flops will cause the active switch 130 to turn off and the cycle is ready to start again.

Let it be assumed that the capacitor C13 has just been discharged, resulting in a zero output from the integrator 157. This zero output appears at the positive terminal of the comparator 148 and the negative input terminal of the comparator 150. Since the negative input terminal of the comparator 148 is receiving a signal more positive than the signal at its positive input terminal, the output of comparator 148 goes to a logic zero. The reference signal to the positive input terminal of the comparator 150 is negative relative to the value of the input signal to the negative input terminal of the comparator 150 thus producing a logic zero at the output of this comparator also. On the next clock pulse, the output of the flip flops 142 and 144 go to a logic zero producing a logic zero at the output of NOR gate 160 which disables the active device 130. Active device 130 may be a transistor switch coupled to a suitable power supply, which switch when conductive provides a driving potential of a polarity opposite to the polarity of the charge on the capacitor C13.

Let it now be assumed that the D.C. component of the input signal to the integrator 157 is negative relative to ground potential. The output of the integrator 157 is a positive going ramp. Under this condition, the input signal to the negative input of the comparator 150 is at all times greater than the reference signal to the positive terminal of this comparator; and therefore, the output of the comparator remains at a logic zero. With respect to comparator 148, the output of this comparator remains at a logic zero so long as the value of the positive going ramp signal remains below the value of the positive reference signal to the negative input terminal of this comparator. As soon as the value of the ramp signal exceeds the reference signal, the output of the comparator changes states. Let it be assumed that a logic 1 appears at the output of the comparator 150. This logic 1 will be transferred to the output of the flip-flop 144 on the occurence on the following clock pulse. The foregoing concerning the operation of the circuit in the presence of a negative level D.C. signal assumes that this D.C. signal will be equal to the full scale voltage.

For signals below the full scale voltage, the inputs to the comparators 148, 150 will not exceed their switch points between successive clock pulses, and therefore, an output bit will not be realized for every two clock pulses. It should now become apparent that the maximum frequency of the output signal from the gate 160 will occur for a full scale input. As the input signal level decreases, the frequency of the bit signals from NOR gate 160 decreases in proportion to the ratio between the full scale voltage and the value of the input signal. In other words, for an input signal at half full scale, the frequency of the output signals would be one half the frequency developed at full scale. The quantization bits produced at the output of the gate 160 is provided to a display 48 and an accumulator averager 46.

FIG. 5 is a diagramatic representation of an accumulator-averager which may be used with the present invention. This circuit accepts positive and/or negative counts when it is enabled through the operation of the gates 225. It algebraically processes the bit signals from the digital filter through a counter chain 228. The chain 228 is supplied to displays 229 which may also receive thresholding inputs from a predetermined level setter 230. The displays may be either digital or analog and may display either the value, the value plus the sign, the sign or the exceedance above a predetermined in claim 1 wherein said quantizer-filter means includes integrator means with a time constant circuit set to cause the integrator output to reach a predetermined level in response to a preset input within a time period determined by the period of said clock means, comparator means responsive to the integrator output and a reference signal for producing outputs representative of the relative levels of said integrator output and said reference signal, and flip-flop means coupled to the outputs from said comparator means and responsive to said clock means for generating a pulse output having a frequency proportional to the voltage level of said analog input signal.

6. An apparatus for remote measuring of the ionic bio-electrical potential of mammalian females as defined in claim 5 wherein said clock means includes first and second comparator means one input to each being coupled to a reference potential set at substantially zero potential, a second input to each receiving a signal at a frequency corresponding to the frequency of a noise produced signal component of said analog input signal.

7. A method for remotely measuring the ionic bio-electrical potential of mammalian females for determining ovulation as defined in claim 1 and further comprising the steps of:
 providing a first container for holding an ionic medium;
 providing a second container for holding an ionic medium;
 inserting the first active probe into the ionic medium contained within the first container;
 inserting the second active probe into the ionic medium contained within the second container;
 inserting at least one finger on one hand of the test subject into the ionic medium contained within the first container in a position laterally spaced from a metallic element located on the first active probe means;
 inserting at least one finger on the other hand of the test subject into the ionic medium contained within the second container in a position laterally spaced from a metallic element located on the second active probe means.

8. A method for remotely measuring the ionic bio-electrical potential of mammalian females for determining ovulation as defined in claim 7 and further comprising the steps of:
 amplifying the detected ionic potential signals from the first and second active probes; and
 converting impedance to the signals to the first and second active probes from a relatively high impedance prior to said step of amplifying to a relatively low impedance following said step of amplifying each of the first and second active probes.

9. An apparatus for remote measuring of the ionic bio-electrical potential of mammalian females for determining ovulation comprising:
 first active probe means for detecting an ionic potential;
 second active probe means for detecting an ionic potential;
 circuits means including an analog to digital quantizer-filter means for generating a probe frequency modulated output in response to an analog input signal from said active probe means, said frequency modulated output being proportional to said analog input signal and clock means responsive to the outputs from said first and second active probes for generating a pulse signal output having a frequency proportional to the frequency of a noise produced component of said analog input signal.

10. An apparatus for remote measuring of the ionic bio-electrical potential of mammalian females as defined in claim 9 wherein:
 said first active probe means includes first preamplifier means mounted upon said probe adjacent a first metallic element located on said first active probe means for amplifying analog electrical signals from said first metallic element; and said second active probe means includes second preamplifier means mounted upon said probe adjacent a second metallic element located on said second active probe means for amplifying analog electrical signals from said second probe element.

11. An apparatus for remote measuring of the ionic bio-electrical potential of mammalian females as defined in claim 10 wherein:
 each of said first and second preamplifier means comprises an operational amplifier and an input impedance means associated with said operational amplifier for presenting a high input impedance to said preamplifier means each of said preamplifier means having an output with a relative low impedance compared to its input impedance.

12. An apparatus for remote measuring of the ionic bio-electrical potential of mammalian females as defined in claim 11 and further comprising:
 a metallic ring means electrically isolated from but surrounding each of said first and second active probe means; and
 conductor means connecting the output of each of said preamplifier means to the respective one of said metallic ring means.

13. An apparatus for remote measuring of the ionic bioelectrical potential of mammalian females as defined in claim 10 wherein said circuit means includes:
 differential amplifier means connected to the output of each said first and second preamplifier means for converting a double ended signal from said first and second active probe means to a single ended signal.

14. An apparatus for remote measuring of the ionic bioelectrical potential of mammalian females as defined in claim 9 wherein said quantizer-filter means includes integrator means with a time constant circuit set to cause the integrator output to reach a predetermined level in response to preset input within a time period determined by the period of said clock means, comparator means responsive to the integrator output said comparator means also being responsive to and a reference signal for producing outputs representative of the relative levels of the inputs thereto said integrator output and said reference signal, and flip-flop means coupled to the outputs from said comparator means and responsive to said clock means for generating a pulse output having a frequency proportional to the voltage level of said analog input signal.

15. An apparatus for remote measuring of the ionic bio-electrical potential of mammalian females as defined in claim 14 wherein said clock means includes first and second comparator means one input to each being coupled to a reference potential set at substantially zero potential, a second input to each receivng a signal at a frequency corresponding to the frequency of a noise produced component of said analog input signal.

16. An apparatus for remote measuring of the ionic bioelectrical potential of mammalian females as defined in claim 9 wherein there includes:
first container means for holding an ionic medium and for receiving said first active probe means and at least one finger on one hand of test subject in a position spaced from said first active probe means;
second container means for holding an ionic medium and for receiving the said second active probe means and at least one finger on the other hand of the test subject in a position spaced from said second active probe means.

17. A method for remotely measuring the ionic bioelectrical potential of mammalian females for determining ovulation comprising the steps of:
detecting an ionic potential
converting the detected ionic potential through an analog to digital quantizer to produce a probe frequency modulated output, and
generating a pulse signal output from a clock signal source having a frequency proportional to the frequency of a noise produced component of the detected ionic potential, and applying said pulse signal output to said analog to digital quantizer as its clock signal,
wherein there is produced a digitized signal proportional to said detected ionic potential devoid of said noise produced component.

* * * * *